United States Patent

Gallenkamp et al.

Patent Number: 4,824,960
Date of Patent: Apr. 25, 1989

[54] PREPARATION OF 1-ARYL-5-AMINO-PYRAZOLES

[75] Inventors: Bernd Gallenkamp; Hermann Arold, both of Wuppertal, Fed. Rep. of Germany

[73] Assignee: Bayer Aktiengesellschaft, Leverkusen, Fed. Rep. of Germany

[21] Appl. No.: 34,300

[22] Filed: Apr. 3, 1987

[30] Foreign Application Priority Data

Apr. 17, 1986 [DE] Fed. Rep. of Germany ....... 3612939

[51] Int. Cl.$^4$ .............................................. C07D 231/38
[52] U.S. Cl. ...................................... 548/362; 546/279
[58] Field of Search ......................... 548/362; 546/279

[56] References Cited

FOREIGN PATENT DOCUMENTS 0167028  1/1986  European Pat. Off. .
1065850  9/1959  Fed. Rep. of Germany .
2701316  7/1978  Fed. Rep. of Germany .

OTHER PUBLICATIONS

Schmidt et al., "Heilmittelchemische Studien in der heterocyclischen Reihe", Helv. Chim. Acta, 41 (1958) pp. 306–309.

Primary Examiner—Robert W. Ramsuer
Attorney, Agent, or Firm—Sprung Horn Kramer & Woods

[57] ABSTRACT

A process for the preparation of a 1-aryl-5-amino-pyrazole of the formula

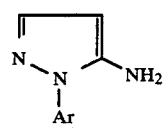

in which
Ar is in each case optionally substituted phenyl or pyridyl, comprising reacting an arylhydrazine of the formula

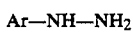

Ar—NH—NH$_2$ with acrylonitrile of the formula

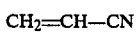

CH$_2$=CH—CN in a first stage in the presence of a diluent at a temperature between about 20° C. and 100° C. to form the arylhydrazine derivative of the formula

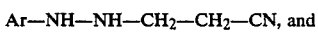

Ar—NH—NH—CH$_2$—CH$_2$—CN, and in a second stage contacting such derivative with an oxidizing agent in the presence of a base at a temperature between about 0° C. and 60° C., thereby to effect oxidation and cyclization. The products are known intermediates for herbicides and insecticides.

10 Claims, No Drawings

PREPARATION OF 1-ARYL-5-AMINO-PYRAZOLES

The invention relates to a new process for the preparation of known 1-aryl-5-amino-pyrazoles which can be used as intermediate products for the synthesis of compounds with a herbicidal and insecticidal activity.

It is already known that 1-aryl-5-amino-pyrazoles are obtained by reacting arylhydrazines with 2,3-dibromopropionitrile or α-chloroacrylonitrile (compare J. Prakt. Chem., 321, 93 (1979); DE-OS (German Published Specification) 2,701,316 and DD-OS (East German Published Specification) 126,303). However, the disadvantages of this process are the high cost and the poor availability of the 2,3-dibromopropionitrile and α-chloroacrylonitrile required as reaction components. Furthermore, the high salt content obtained in the reaction mixture during the course of the reaction, in particular, has an extremely adverse effect on the process procedure.

It is furthermore known that 1-aryl-5-amino-pyrazoles are obtained by reacting arylhydrazines with cyanoacetylene (compare Takedo Kenkyusho Ho, 1971, 30, 475 [CA: 76: 85737 (1972)]). The disadvantages of this are again the high cost and the unavailability of the cyanoacetylene required as a reaction component.

It is moreover known that 1-aryl-5-amino-pyrazoles are obtained by reacting arylhydrazines with β-dimethylaminoacrylonitrile (compare Helv., Chim Acta, 48, 1754 and DE-OS (German Published Specification) 2,141,700).

The high cost and the poor availability of the β-dimethylaminoacrylonitrile are again a disadvantage.

It is also known that 1-aryl-5-amino-pyrazoles are obtained by converting isoxazole into cyanoacetaldehyde in an alkaline medium, subsequently condensing the cyanoacetaldehyde with arylhydrazines in an acid medium to give the arylhydrazones of cyanoacetaldehyde and finally cyclizing these in an alkaline medium (compare Chem. Ber. 42, 59, (1909)). The disadvantages of this process are the poor overall yield and the general disadvantages of a multi-stage reaction procedure.

Finally, it is known that 1-aryl-5-amino-pyrazoles are obtained by reacting malonodialdehyde dioxime with nitrous acid and an arylhydrazine (compare Liebigs Ann. 739, 139 (1969) and DE-OS (German Published Specification) 1,913,845). The disadvantages of this process are the high cost and the poor availability of the malonodialdehyde dioxime required as a reaction component.

It has now been found that known 1-aryl-5-aminopyrazoles of the general formula (I)

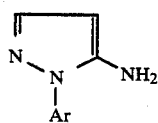

(I)

in which Ar represents in each case optionally substituted phenyl or pyridyl, are obtained by a process in which arylhydrazines of the formula (II)

Ar—NH—NH$_2$     (II)

in which Ar has the abovementioned meaning, are initially reacted with acrylonitrile of the formula (III)

CH$_2$=CH—CN     (III)

in a first stage in the presence of a diluent and if appropriate in the presence of a catalyst, at temperatures between 20° C. and 100° C. to give the arylhydrazine derivatives of the formula (IV)

AR—NH—NH—CH$_2$—CH$_2$—CN     (IV)

in which Ar has the abovementioned meaning, and, if appropriate after intermediate isolation, these are oxidized and cyclized in a second stage in the presence of diluent and in the presence of an oxidizing agent, such as, for example, sodium hypochlorite, hydrogen peroxide or oxygen, and in the presence of a base at temperatures between 0° C. and 60° C.

It is to be described as decidedly surprising that the oxidation of the arylhydrazine derivatives of the formula (IV) in the presence of such a weak oxidizing agent such as, for example, air and the cyclization in the presence of a base succeed in such good yields, since such reactions are known from the prior art only in the presence of powerful oxidizing agents, such as iron salts (compare Helv. Chim. Acta, 41, 306 (1958)).

The process according to the invention is distinguished by a number of advantages. Thus, it enables 1-aryl-5-aminopyrazoles to be prepared in high yields and in a high purity, the starting substances being readily available. Furthermore, the reaction is extremely easy and economical to carry out in a one-pot process. Isolation of the 1-aryl-5-amino-pyrazoles presents no difficulties at all, whereas working up of the reaction mixture in the case of oxidation by iron salts is made extremely troublesome by the precipitates which are difficult to separate off.

1-Aryl-5-amino-pyrazoles which are preferably obtained with the aid of the process according to the invention are those of the formula (I)

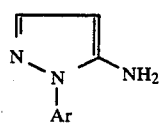

(I)

in which Ar represents phenyl which is monosubstituted by polysubstituted by identical or different substituents, or represents 2-pyridyl, 3-pyridyl or 4-pyridyl, in each case optionally monosubstituted or polysubstituted by identical or different substituents, possible substituents in each case being: cyano, nitro, halogen, in each case straight-chain or branched alkyl, alkoxy and alkoxycarbonyl with in each case 1 to 4 carbon atoms in the alkyl part and also in each case straight-chain or branched halogenoalkyl and halogenoalkoxy with in each case 1 to 4 carbon atoms and 1 to 9 identical or different halogen atoms, and a radical

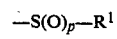

—S(O)$_p$—R$^1$ wherein R$^1$ represents amino, or represents in each case straight-chain or branched alkyl, alkylamino, dialkylamino or halogenoalkyl with in each case 1 to 4 carbon atoms in the individual alkyl parts and, in the case of the halogenoalkyl, with 1 to 9 identical or different halogen atoms and p represents the number 0, 1 or 2.

The process according to the invention particularly preferably relates to compounds of the formula (I) in which Ar represents phenyl which is mono-, di-, tri-, tetra- or pentasubstituted by identical or different substituents, or represents 2-pyridyl or 4-pyridyl, in each case optionally mono-, di-, tri- or tetrasubstituted by identical or different substituents, possible substituents on the phenyl or pyridyl in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical

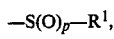

wherein $R^1$ represents amino, methylamino, ethylamino, dimethylamino, diethylamino, fluorodichloromethyl, difluorochloromethyl, tetrafluoroethyl, trifluorochloroethyl, trifluoromethyl, methyl or ethyl and p represents the number 0, 1 or 2.

If, for example, 2,6-dichloro-4-trifluoromethylphenylhydrazine and acrylonitrile are used as starting substances, oxygen is used as the oxidizing agent and sodium hydroxide is used as the base, the course of the process according to the invention can be illustrated by the following equation:

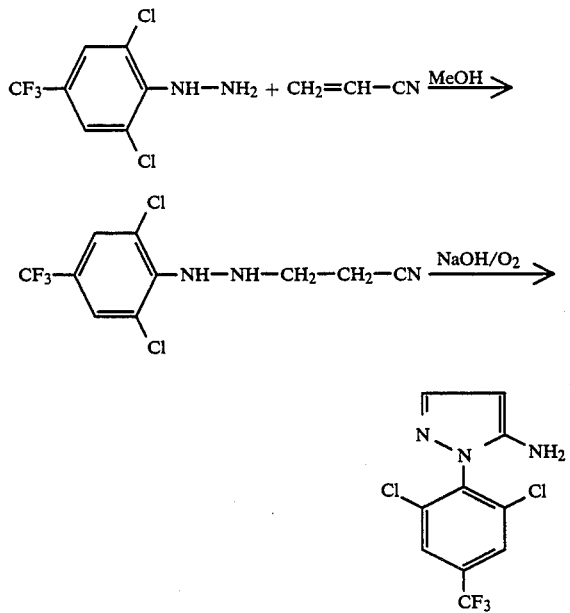

Formula (II) provides a general definition of the arylhydrazines required as starting substances for carrying out the process according to the invention. In this formula (II), Ar preferably represents those radicals which have already been mentioned as preferred for these substituents in connection with the description of the end products of the formula (I).

The arylhydrazines of the formula (II) are known (compare, for example, U.S. Pat. No. 4,127,575; U.S. Pat. No. 3,609,158; DE-OS (German Published Specification) 2,558,399; and J. Chem. Soc. C 1971, 167), or they can be prepared by known processes in a simple, analogous manner (compare: for example Houben-Weyl "Methoden der organischen Chemie" ("Methods of Organic Chemistry") Volume X/2, page 203, Thieme Verlag Stuttgart 1967), for example by reacting the corresponding amines with sodium nitrite in the presence of an acid, such as, for example, sulphuric acid, and then reacting the product with tin(II) chloride, likewise in the presence of an acid, such as, for example, hydrochloric acid, at temperatures between −20° C. and +80° C.

The acrylonitrile of the formula (III) is a generally known compound of organic chemistry.

The process according to the invention is carried out in the presence of a diluent. Diluents include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide. Ethanol or methanol is particularly preferably used as the solvent.

The reaction temperatures can be varied within a substantial range in carrying out the process according to the invention. The reaction in the first stage is in general carried out at temperatures between 20° C. and 100° C., preferably at temperatures between 40° C. and 80° C. In the second stage, the reaction is in general carried out at temperatures between 0° C. and 60° C., preferably at temperatures between 10° C. and 50° C.

If appropriate, the first stage of the process according to the invention can be carried out in the presence of a catalyst, and it is preferably carried out in the presence of a catalyst. Catalysts include, preferably, disodium salt of ethylendiaminetetraacetic acid (Titriplex III), alanine or benzyltrimethylammonium hydroxide (Triton B).

The second stage of the process according to the invention requires the presence of an oxidizing agent. Sodium hypochlorite, hydrogen peroxide or atmospheric oxygen is particularly suitable.

The second stage of the process according to the invention is carried out in the presence of a base. Bases include, preferably, alkali metal hydroxides, such as, for example, sodium hydroxide and potassium hydroxide, and alkali metal alcoholates, such as, for example, sodium methylate and potassium methylate.

The process according to the invention is in general carried out under normal pressure, but it can also be carried out under increased or reduced pressure, for example between 0.1 and 10 bar.

For carrying out the process according to the invention, in general 1 to 5 mols, preferably 1 to 3 mols, of acrylonitrile are employed in the first stage, per mol of arylhydrazine of the formula (II), and in general 1 to 4 mol, preferably 1 to 3 mols, of oxidizing agent and in general 0.1 to 1 mol, preferably 0.4 to 0.5 mol, of base are employed in the second stage.

The reaction is carried out by a procedure in which the reaction partners are heated in the corresponding diluent and if appropriate in the presence of a catalyst for 24 to 48 hours and, if appropriate after intermediate isolation, the product is then reacted in the presence of the corresponding oxidizing agent, the corresponding base and the corresponding diluent at temperatures between 20° C. and 40° C. for 6 to 12 hours.

The 1-aryl-5-amino-pyrazoles of the formula (I) are isolated in the customary manner, for example by a procedure in which the reaction mixture is rendered neutral and concentrated, the residue is extracted with a water-insoluble organic solvent, the extract is washed with water and dried and the organic solvent is removed by distillation.

The 1-aryl-5-amino-pyrazoles of the formula (I) which can be prepared by the process according to the invention are known starting substances for the synthesis of biologically active compounds, such as, for example, for the synthesis of substituted 5-amino-1-phenyl-pyrazoles which have good herbicidal properties. When applied in appropriate amounts, the 1-aryl-5-amino-pyrazoles which can be prepared by the process according to the invention themselves also have a herbicidal action (compare U.S. Pat. No. 4,614,533).

Thus, for example, 5-propionamido-1-(2,6-dichloro-4-trifluoromethylphenyl)-pyrazole of the formula

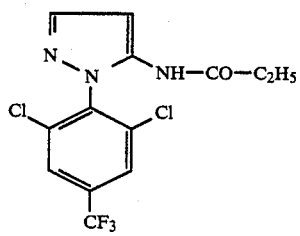

can be prepared by a process in which 5-amino-1-(2,6-dichloro-4-trifluoromethylphenyl)-pyrazole is reacted with propionyl chloride in the presence of methylene chloride and pyridine. This synthesis can be illustrated by formulae as follows:

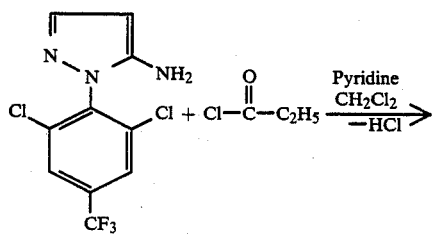

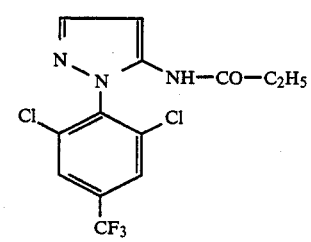

The process according to the invention is illustrated by the following examples.

Example 1

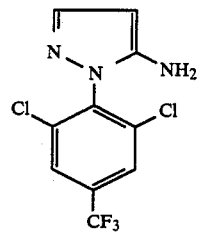

(Stage 1 and 2 as a one-pot process)

245 g (1 mol) of 2,6-dichloro-4-trifluoromethylphenylhydrazine, 60 g (1.14 mol) of acrylonitrile and 1 g of disodium salt of ethylendiaminetetraacetic acid (Titriplex III) are heated under reflux in 350 ml of methanol for 24 hours. 20 g of sodium hydroxide are then added and air is passed through the reaction mixture at 20° C. for 10 hours. Thereafter, the reaction mixture is brought to pH 7 with concentrated hydrochloric acid and is concentrated, the residue is taken up in 250 ml of toluene and the mixture is washed twice with 500 ml of water each time. The organic phase is concentrated and distilled.

281 g (95% of theory) of 1-(2,6-dichloro-4-trifluoromethylphenyl)-5-amino-pyrazole of melting point 90°–94° C. are obtained.

Preparation of the starting compound:

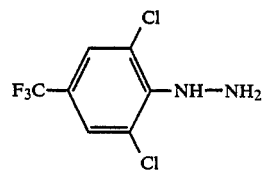

6.2 g (0.025 mol) of 3,4,5-trichloro-trifluoromethylbenzene and 6.25 g (0.125 mol) of hydrazine hydrate are heated under reflux at 115°–120° C. in 12 ml of pyridine for 48 hours. For working up, the solvent is distilled off, the residue is taken up in water and the mixture is extracted three times with about 30 ml of methylene chloride each time. The combined organic phases are dried over magnesium sulphate and concentrated in vacuo and the residue is then distilled.

5.1 g (83% of theory) of 2,6-dichloro-4-trifluoromethylphenylhydrazine of melting point 56° to 57° C. with a content, determined by gas chromatography, of 90% are obtained.

Example 2

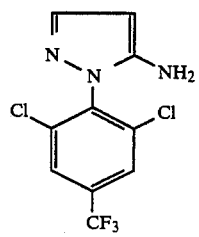

Stage 2

38 g of sodium hypochlorite solution (prepared by passing about 18 g of chlorine into 220 g of 20% strength sodium hydroxide solution) are added dropwise to 13.5 (0.04 mol) of N-(2,3,6-trichloro-4-trifluoromethylphenyl)-N'-2-cyano-ethylhydrazine in 80 ml of ethanol at 10° C. The mixture is stirred at 20° C. for 16 hours, 0.5 g of solid sodium hydroxide are added and the mixture is subsequently stirred for 6 hours. It is concentrated, the residue is taken up in methylene chloride, the mixture is washed twice with water and concentrated and the residue is distilled. 10 g (76% of theory) of 1-(2,3,6-trichloro-4-trifluoromethylphenyl)-5-amino-pyrazole are obtained.

$^1$H-NMR (CDCl$_3$): δ=7.85 (1H); 7.55, 5.7 (2H); 3.6 (2H).

Preparation Example for a herbicidally active compound

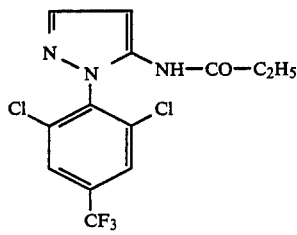

5 ml (5.3 g/0.05 mol) of 98% pure propionyl chloride and then 5 ml (5.0 g/0.063 mol) of anhydrous pyridine are added in succession to 14.8 g (0.05 mol) of 5-amino-1-(2,6-dichloro-4-trifluoromethylphenyl)-pyrazole in 100 ml of methylene chloride at room temperature, while stirring. The temperature thereby increases to 40° C. When the addition has ended, stirring is continued at room temperature for 16 hours, 50 ml of methylene chloride are added, the mixture is washed in each case twice with 100 ml of water, 100 ml of saturated sodium bicarbonate solution and 100 ml of sodium chloride solution and dried over magnesium sulphate and the solvent is removed in vacuo. The solid residue is washed with a little hexane and dried.

12.2 g (69.3% of theory) of 5-propionamido-1-(2,6-dichloro-4-trifluoromethylphenyl)-pyrazole of melting point 125° C. are obtained.

It will be understood that the specification and examples are illustrative but not limitative of the present invention and that other embodiments within the spirit and scope of the invention will suggest themselves to those skilled in the art.

What is claimed is:

1. A process for the preparation of a 1-aryl-5-amino-pyrazole of the formula

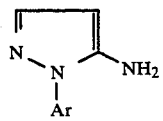

in which Ar is in each case optionally substituted phenyl or pyridyl, comprising reacting an arylhydrazine of the formula

with acrylonitrile of the formula

in a first stage in the presence of a diluent at a temperature between about 20° C. and 100° C. to form the arylhydrazine derivative of the formula

in a second stage contacting such derivative with an oxidizing agent selected from the group consisting of sodium hypochlorite and atmospheric oxygen in the presence of a base at a temperature between about 0° C. and 60° C., thereby to effect oxidation and cyclization.

2. A process according to claim 1, wherein the disodium salt of ethylendiaminetetraacetic acid (Titriplex III), alanine or benzyltrimethylammoniumhydroxide (Triton B) is used as a catalyst in the first stage.

3. A process according to claim 1, wherein an alkali metal hydroxide or alkali metal alcoholate is used as the base in the second stage.

4. A process according to claim 1, wherein the first stage is carried out at a temperature between about 40° C. and 80° C.

5. A process according to claim 1, wherein the second stage is carried out at a temperature between about 10° C. and 50° C.

6. A process according to claim 1, wherein per mol of arylhydrazine about 1 to 5 mols of acrylonitrile are employed in the first stage, and about 1 to 4 mols of oxidizing agent and about 0.1 to 1 mol of base are employed in the second stage.

7. A process according to claim 1, wherein the second stage is effected without isolation of the product of the first stage.

8. A process according to claim 1, in which
Ar is phenyl or pyridyl which are unsubstituted or substituted by substituents independently selected from the group consisting of cyano, nitro, halogen, alkyl, alkoxy, alkoxycarbonyl, halogenoalkyl, halogenoalkoxy, and the radical

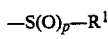

wherein
R$^1$ is amino, alkyl, alkylamino, di-alkylamino or halogenoalkyl, and
p is 0, 1 or 2,
the alkyl moieties in Ar and R$^1$ when present having 1 to 4 carbon atoms.

9. A process according to claim 8, wherein the disodium salt of ethylendiaminetetraacetic acid (Titriplex III), alanine or benzyltrimethylammoniumhydroxide (Triton B) is used as a catalyst in the first stage which is carried out at a temperature between about 40° C. and 80° C., sodium hypochlorite or atmospheric oxygen is used as the oxidizing agent and an alkali metal hydroxide or alkali metal alcoholate is used as the base in the second stage which is carried out at a temperature between about 10° C. and 50° C. without isolation of the product of the first stage, about 1 to 5 mols of acrylonitrile, 1 to 4 mols of oxidizing agent and about 0.1 to 1 mol of base being employed per mol of arylhydrazine.

10. A process according to claim 1, wherein the oxidizing agent is atmospheric oxygen.

* * * * *